(12) United States Patent
Quinn et al.

(10) Patent No.: US 9,357,930 B2
(45) Date of Patent: Jun. 7, 2016

(54) TEMPERATURE MEASUREMENT SYSTEM

(75) Inventors: David E. Quinn, Auburn, NY (US);
John A. Lane, Weedsport, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 499 days.

(21) Appl. No.: 13/423,814

(22) Filed: Mar. 19, 2012

(65) Prior Publication Data
US 2013/0245488 A1    Sep. 19, 2013

(51) Int. Cl.
*A61B 5/01*     (2006.01)
*A61B 5/00*     (2006.01)
*G01J 5/02*     (2006.01)

(52) U.S. Cl.
CPC .............. *A61B 5/01* (2013.01); *A61B 5/6817* (2013.01); *G01J 5/021* (2013.01); *A61B 2562/247* (2013.01)

(58) Field of Classification Search
CPC .......... A61B 5/01; A61B 5/6817; G01J 5/021
USPC ............ 600/549, 473; 250/331; 374/100, 101
See application file for complete search history.

(56) References Cited

U.S. PATENT DOCUMENTS

| | | | |
|---|---|---|---|
| 4,602,642 A | 7/1986 | O'Hara et al. | |
| 4,846,236 A * | 7/1989 | Deruntz | 141/329 |
| 5,017,018 A | 5/1991 | Iuchi et al. | |
| 5,046,482 A | 9/1991 | Everest | |
| 5,159,936 A | 11/1992 | Yelderman et al. | |
| 5,172,978 A | 12/1992 | Nomura et al. | |
| 5,368,038 A | 11/1994 | Fraden | |
| 5,411,032 A * | 5/1995 | Esseff et al. | 600/549 |
| 5,445,158 A | 8/1995 | Pompei | |
| 5,795,067 A * | 8/1998 | Fraden | G01J 5/02 374/158 |
| 5,833,367 A | 11/1998 | Cheslock et al. | |
| 5,938,590 A * | 8/1999 | Elliott | 600/184 |
| 6,001,006 A | 12/1999 | Pineau et al. | |
| 6,001,066 A * | 12/1999 | Canfield et al. | 600/559 |
| 6,149,297 A | 11/2000 | Beerwerth et al. | |
| 6,156,148 A | 12/2000 | Beerwerth et al. | |
| 6,195,581 B1 * | 2/2001 | Beerwerth et al. | 600/474 |
| 6,332,090 B1 * | 12/2001 | DeFrank et al. | 600/474 |
| 6,347,243 B1 * | 2/2002 | Fraden | 600/474 |

(Continued)

FOREIGN PATENT DOCUMENTS

JP       06066638 A  *  3/1994
JP    2000139850 A     5/2000

(Continued)

OTHER PUBLICATIONS

Rhoads et al., Assessment of an aural infrared sensor for body temperature measurement in children, Clin Pediatr (Phila). Feb. 1990; 29(2); 112-5.

(Continued)

*Primary Examiner* — Sean Dougherty

(57) ABSTRACT

A temperature measurement system includes a temperature probe having a head and an infrared temperature sensor disposed in the head. The system also includes a replaceable probe cover removably attachable to the head. The probe cover includes a body, a substantially cylindrical waveguide extending from the body, and a distal tip. The waveguide is configured to direct radiation entering the distal tip to the temperature sensor when the probe cover is attached to the head.

23 Claims, 5 Drawing Sheets

(56) References Cited

U.S. PATENT DOCUMENTS

| | | | |
|---|---|---|---|
| 6,371,925 B1* | 4/2002 | Imai et al. | 600/549 |
| 6,386,757 B1 | 5/2002 | Konno | |
| 6,435,712 B1* | 8/2002 | Ota | 374/131 |
| 6,595,317 B1* | 7/2003 | Widmer et al. | 181/135 |
| 6,789,936 B1* | 9/2004 | Kraus | G01J 5/0022 374/121 |
| 7,237,949 B2* | 7/2007 | Lantz et al. | 374/158 |
| 7,815,367 B2* | 10/2010 | Lane et al. | 374/121 |
| RE43,745 E * | 10/2012 | Walker et al. | 374/158 |
| 8,517,603 B2* | 8/2013 | Fraden | 374/121 |
| 2001/0014112 A1* | 8/2001 | Yamaka | 374/158 |
| 2006/0159155 A1* | 7/2006 | Lantz | G01J 5/00003 374/158 |
| 2006/0165152 A1* | 7/2006 | Walker et al. | 374/158 |
| 2007/0263698 A1* | 11/2007 | Lin et al. | 374/158 |
| 2008/0089387 A1* | 4/2008 | Price | 374/158 |
| 2008/0173315 A1* | 7/2008 | Falco | 128/864 |
| 2009/0129437 A1* | 5/2009 | Chuang et al. | 374/158 |
| 2009/0154748 A1* | 6/2009 | Baker et al. | 381/328 |
| 2009/0287147 A1* | 11/2009 | Wenchell et al. | 604/99.04 |
| 2010/0284436 A1 | 11/2010 | Lane et al. | |
| 2011/0134962 A1* | 6/2011 | Fraden | 374/209 |
| 2011/0257521 A1* | 10/2011 | Fraden | 600/438 |
| 2012/0076169 A1* | 3/2012 | Hsieh | 374/158 |
| 2013/0085707 A1* | 4/2013 | Holderle et al. | 702/130 |
| 2013/0202011 A1* | 8/2013 | Mullin et al. | 374/158 |

FOREIGN PATENT DOCUMENTS

| | | | |
|---|---|---|---|
| JP | 2000210262 A | * | 8/2000 |
| JP | 2000342540 A | * | 12/2000 |
| JP | 2001128943 A | | 5/2001 |
| WO | WO02/073144 A1 | | 9/2002 |

OTHER PUBLICATIONS

Genius 2 Tympanic Thermometer Complete with Base, http://www.safehomeproducts.com/shp2/product/genius-2-tympanic-thermometer-complete-with-base/covers/268140/268140.aspx ; accessed Mar. 22, 2012.

Ear Thermometry, http://www.exergen.com/medical/product/LTXhome1.htm ; accessed Mar. 22, 2012.

International Search Report and Written Opinion, mailed Jun. 28, 2013, PCT/US2013/032266, 12 pages.

* cited by examiner

TEMPERATURE MEASUREMENT SYSTEM

FIELD OF THE INVENTION

The present disclosure relates to systems and methods for temperature determination and, in particular, to systems and methods for determining a patient's core temperature.

BACKGROUND OF THE INVENTION

Measuring patient temperature is a common first step in diagnosing illnesses. Physicians commonly use a variety of methods for determining patient temperature including, for example, obtaining temperature measurements with a thermometer. While thermometers utilizing mercury have been in existence for many years, modern thermometers typically employ one or more electronic sensors configured to measure patient temperature. Such sensors may take one or more measurements over a relatively short period of time. Based on these measurements, the thermometer may generate an estimated internal and/or core temperature of the patient. In generating this estimated core temperature, it is common practice to insert at least a portion of the thermometer into a cover prior to taking temperature measurements. The cover may overlay the electronic temperature sensor of the thermometer, and may protect the sensor from contamination during use.

Determining core temperature in this way may, however, be difficult depending on the age and/or physical characteristics of the patient. For example, while standard thermometers and covers may be sized for insertion into an average adult ear canal, such instruments may not be suitable for use with patients having ear canals that have dimensions different than that of the average adult. In particular, such instruments may be too large for use with infants and pediatric patients having ear canals smaller than the average adult ear canal. Such instruments may also be difficult to use with geriatric patients having partially closed or blocked ear canals. While one solution to these difficulties may be to use thermometers of different sizes and/or configurations for such different patients, physicians may not be in favor of such an approach due to the added cost and inconvenience associated with the use of multiple different thermometers.

The exemplary embodiments of the present disclosure are directed toward overcoming the deficiencies described above.

SUMMARY

In an exemplary embodiment of the present disclosure, a temperature measurement system includes a temperature probe having a head and an infrared temperature sensor disposed in the head. The system also includes a replaceable probe cover removably attachable to the head. The probe cover includes a body, a substantially cylindrical waveguide extending from the body, and a distal tip. The waveguide is configured to direct radiation entering the distal tip to the temperature sensor when the probe cover is attached to the head.

In another exemplary embodiment of the present disclosure, a temperature measurement system includes a probe cover configured for use with a temperature probe having an infrared temperature sensor. The probe cover includes a hollow substantially conical body having a central longitudinal axis, a substantially cylindrical waveguide extending from the body along the longitudinal axis, and a substantially atraumatic distal tip. The waveguide includes an inner wall and an infrared reflective material disposed on the inner wall. The infrared reflective material is configured to direct radiation entering the distal tip to the temperature sensor.

In a further exemplary embodiment of the present disclosure, a method of determining a temperature of a patient includes attaching a removable probe cover to a head of a temperature probe, and inserting a waveguide at a distal end of the probe cover into an ear canal of the patient. The method also includes collecting infrared radiation passing from a tympanic membrane of the patient to a sensor disposed within the head of the temperature probe. A portion of the infrared radiation is directed to the sensor upon reflecting off of an inner wall of the waveguide. The method further includes determining the temperature of the patient based on the collected radiation.

DETAILED DESCRIPTION

Figure 1:
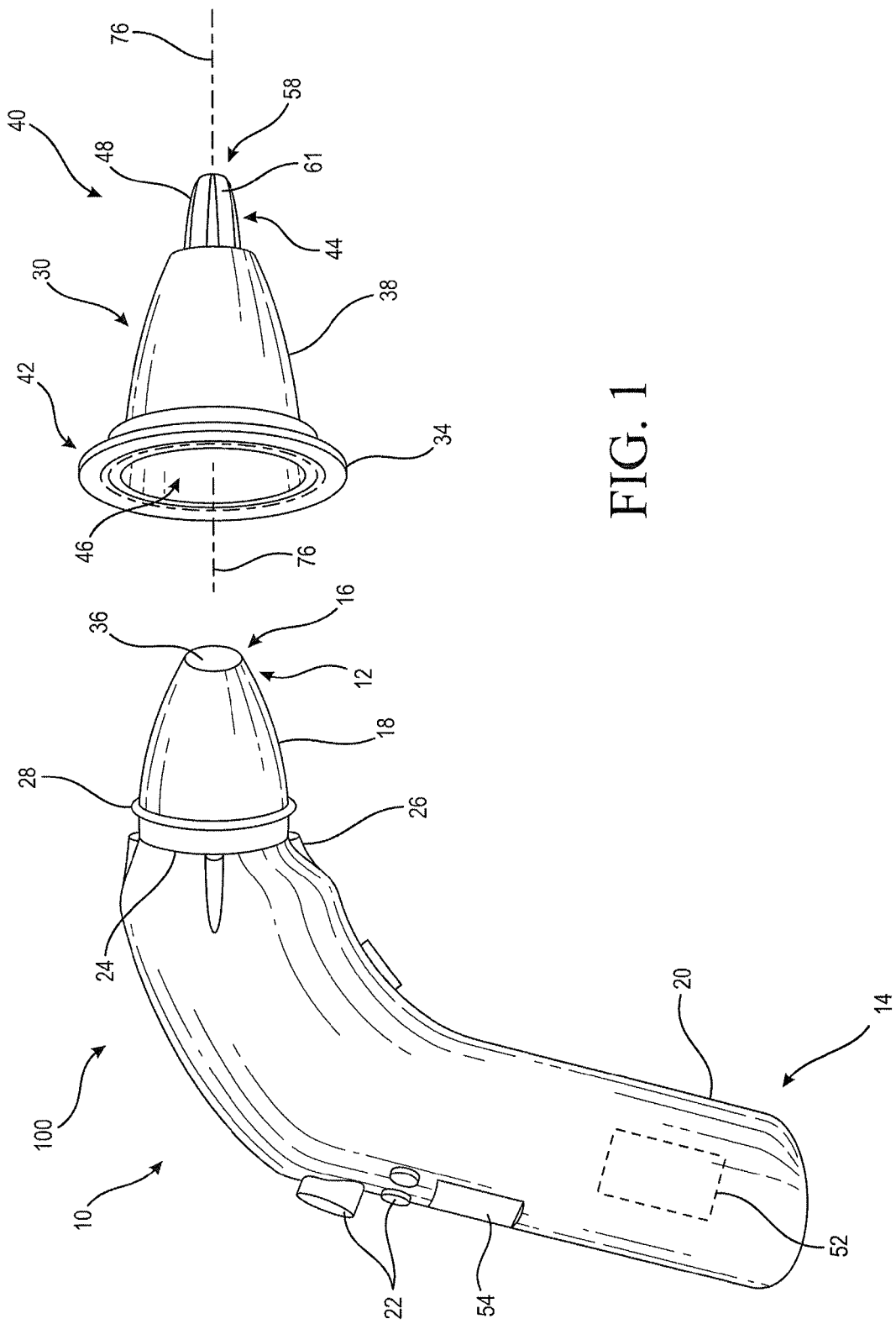
FIG. 1 illustrates a temperature measurement system according to an exemplary embodiment of the present disclosure.

FIG. 1 illustrates an exemplary temperature measurement system 100 of the present disclosure including a temperature probe 10 and a corresponding probe cover 30. The temperature probe 10 may include, for example, a head 18 connected to a handle 20. The head 18 may define a distal end 12 of the temperature probe 10, and the handle 20 may define a proximal end 14 of the probe 10. The head 18 may include an atraumatic tip 16 disposed at the distal end 12. The tip 16 may be sufficiently rounded and/or otherwise configured so as not to cause injury to a patient upon contact with a body surface or at least partial insertion of the head 18 within one or more body cavities of the patient. In an exemplary embodiment in which the temperature probe 10 is utilized to measure, calculate, estimate and/or otherwise determine a core temperature of the patient, it is understood that such body cavities may include the ear, mouth, rectum, underarm, and/or other known body cavities from which temperature may be sensed. It is understood that the implementation of the disclosed technology in a temperature probe 10 is merely exemplary. The disclosed technology may be applicable to any other medical device that may use a cover, sheath, and/or other structure to protect the device from contaminants present on a surface or in a cavity of the body. Such medical devices may include, for example, probes, endoscopes, speculums, and/or other like devices where the characteristics of the cover/sheath impact the accuracy or precision of data gathered or measurements taken by the medical device.

The head 18 and/or the handle 20 may be made from any material and/or combinations of materials commonly used in medical and/or examination procedures. Such materials may include, for example, plastics, polymers, composites, stainless steel, alloys, and/or any other like materials. Such materials may be suitable for repeated use and/or repeated sanitation. Accordingly, in an exemplary embodiment of the present disclosure, the temperature probe 10 and/or its components may be substantially waterproof. One or more waterproof seals may be included and/or otherwise utilized with components of the temperature probe 10 to facilitate such repeated sanitation and/or use.

The handle 20 may include one or more operator interfaces 22. Such operator interfaces 22 may be configured to assist in performing one or more functions of the temperature probe 10. For example, the operator interfaces 22 may comprise any combination of switches, buttons, levers, knobs, dials, keys, and/or other like components configured to activate, deactivate, manipulate, and/or otherwise control components of the temperature probe 10. Such operator interfaces 22 may, for example, assist the user in toggling through and/or selecting one or more modes of operation of the temperature probe 10, enabling and/or disabling one or more alarms or signals associated with operation of the probe 10, initiating a single substantially instantaneous temperature calculation, initiating a substantially continuous and/or repeating temperature calculation, and/or other like modes, functions, or operations.

In an exemplary embodiment, at least one of the operator interfaces 22 may be operably connected to an ejector mechanism 26 disposed proximate a base 24 of the head 18. At least a portion of the temperature probe 10 may be inserted into the probe cover 30 before and/or during use, and such an ejector mechanism 26 may be configured to assist in removing the probe cover 30 from the temperature probe 10. For example, the ejector mechanism 26 may comprise one or more fingers, hooks, shoulders, arms, tabs, rings, and/or other like structures configured to assist in ejecting the probe cover 30 from the base 24 of the head 18 after use. In an exemplary embodiment, one or more such ejector mechanisms 26 may be movable with respect to the base 24 and/or the head 18. In such exemplary embodiments, the ejector mechanisms 26 may be movable in, for example, a path substantially parallel to the head 18. In additional exemplary embodiments, the ejector mechanisms 26 may be movable in an arcuate path relative to the head 18. Movement of the ejector mechanisms 26 may assist in bending, flexing, and/or otherwise deforming at least a portion of the probe cover 30. For example, as will be described below, the ejector mechanisms 26 may be movable along one or more caroming surfaces 84 (FIG. 2) of the probe cover 30, and such movement may assist in flexing at least a portion of the probe cover 30. As will also be described below, such flexing may ultimately overcome a retention force provided by one or more retention components 28, 80 of the temperature probe 10 and/or the probe cover 30, thereby releasing the probe cover 30 from the temperature probe 10.

Figures 2, 3:
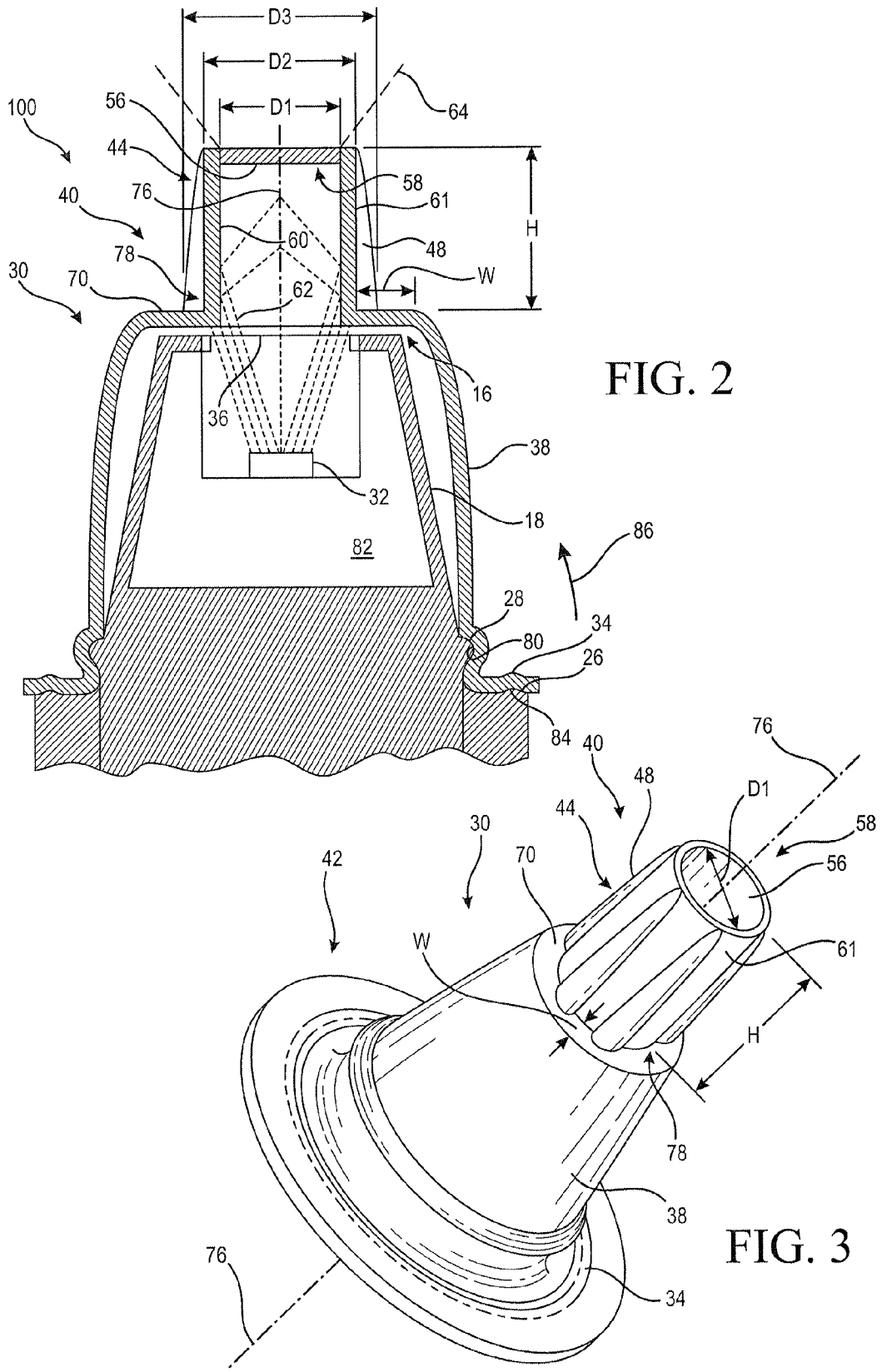
FIG. 2 illustrates a cross-sectional view of a portion of the temperature measurement system shown in FIG. 1.
FIG. 3 illustrates an exemplary probe cover of the present disclosure.

In additional exemplary embodiments, one or more operator interfaces 22 may be configured to assist in controlling one or more corresponding sensors associated with the temperature probe 10. For example, the operator interfaces 22 may be operably connected to at least one sensor 32 (FIG. 2). In exemplary embodiments, the sensor 32 may be embedded within and/or otherwise formed integrally with the head 18 and/or the handle 20. In such exemplary embodiments, it is understood that the sensor 32 may be electrically, operably, and/or otherwise connected to the operator interfaces 22 and/or other components of the temperature probe 10 via known electrical connections. As will be described in greater detail below, the sensor 32 may be operably, controllably, electrically, and/or otherwise connected to a controller 52. In such an exemplary embodiment, the controller 52 may be configured to assist in estimating a core temperature of a patient based on signals and/or other input from the sensor 32.

In an exemplary embodiment, the sensor 32 may be configured to sense one or more physical characteristics of a patient such as, for example, temperature, blood pressure, and the like. In an exemplary embodiment, the sensor 32 may comprise a temperature sensor, such as a thermopile, thermocouple, and/or thermistor, configured to sense a temperature associated with the patient. For example, such a sensor may be configured to sense a temperature of the body cavity into which the temperature probe 10 has been inserted. For example, in embodiments in which the head 18 of the temperature probe 10 is inserted into the ear of the patient, such a sensor 32 may be utilized to sense a temperature associated with the tympanic membrane of the patient.

In an additional exemplary embodiment, the sensor 32 may comprise an infrared temperature sensor such as, for example, a thermopile and/or other like infrared-based temperature sensing components. Such a sensor 32 may be configured to convert thermal energy into electrical energy, and may comprise two or more thermocouples connected in series or in parallel. Such components may be configured to generate an output voltage proportional to a local temperature difference and/or temperature gradient. In an exemplary embodiment in which the sensor 32 comprises at least one thermopile, the temperature probe 10 may comprise, for example, an infrared temperature probe and/or other like infrared thermometer. In such embodiments, the sensor 32 may be configured to receive and/or emit radiation 62, such as thermal and/or infrared radiation. For example, the sensor 32 may be configured to sense, detect, collect, and/or otherwise receive radiation 62 emitted by the patient. Such radiation 62 may be emitted by, for example, the tympanic membrane and/or any other portion of the body cavity within which a portion of the head 18 of the temperature probe 10 is inserted. In such embodiments, the sensor 32 may be configured to collect the radiation 62, and to send a signal to the controller 52 indicative of the collected radiation 62. The controller 52 may utilize the received signal for any number of known functions. For example, the controller 52 may be configured to estimate, infer, calculate, and/or otherwise determine a core temperature of the patient based on the signal.

The sensor 32 may be configured to collect radiation 62 that is reflected, reemitted, and/or otherwise returned to the sensor 32. For example, at least a portion of such radiation 62 may reflect off of the tympanic membrane and/or may be absorbed and reemitted by the membrane. In such embodiments, the sensor 32 may be configured to collect the reflected and/or reemitted radiation 62, and to send a signal to the controller 52 indicative of the collected radiation 62. The controller 52 may be configured to estimate, infer, calculate, and/or otherwise determine a core temperature of the patient based on the signal.

The temperature probe 10 may additionally include at least one window, lens, and/or other like optical component 36 positioned proximate the sensor 32. For example, such an optical component 36 may be disposed substantially flush and/or coplanar with the outer surface of the head 18. Such optical components 36 may be disposed, for example, at the tip 16 of the temperature probe 10, and may be configured to assist in, for example, focusing, directing, and/or otherwise transmitting radiation 62 to the sensor 32 for collection. In additional exemplary embodiments, such optical components 36 may assist in focusing, directing, and/or otherwise transmitting radiation 62 emitted by the sensor 32. Such optical components 36 may also assist in protecting the thermopile, thermocouple, thermister, and/or other sensor components during use of the temperature probe 10, and may assist in forming a substantially fluid tight compartment 82 within the head 18 to protect sensor components from contact with bodily fluids, cleaning solutions, and/or other liquids. It is understood that such optical components 36 may be substantially transparent to assist in the transmission of infrared and/or other types of radiation. In exemplary embodiments, the optical components 36 may comprise one or more convergent, collimating, and/or divergent lenses.

The handle 20 may also include one or more displays 54 operably connected to the controller 52. The display 54 may comprise, for example, a liquid crystal display (LCD) screen, a light emitting diode (LED) display, a digital read-out, and/or any other like components configured to communicate information to the user of the temperature probe 10. Such displays 54 may be configured to indicate, for example, one or more temperatures sensed by the sensor 32, one or more temperatures calculated based on signals received from the sensor 32, and/or any other information that may be useful during operation of the temperature probe 10. The display 54 may be configured to communicate such information substantially instantaneously and/or substantially continuously depending on the mode of operation of the temperature probe 10. Such a display 54 may also indicate whether or not the temperature probe 10 is turned on, and whether a probe cover 30 has been connected to the temperature probe 10. The display 54 may also be configured to indicate the mode of operation of the temperature probe 10 (for example, continuous or instantaneous modes of temperature calculation), as well as whether one or more threshold temperatures, threshold temperature change rates, and/or other sensed metric thresholds have been met or exceeded. The display 54 may be, for example, a substantially numerical digital display, and may also be configured to display any other typical operating information such as, for example a temperature vs. time trend line or other graphical depictions.

The temperature probe 10 may also include one or more signal devices (not shown) operably connected to the controller 52. Such signal devices may include, for example, one or more lights, LEDs, speakers, and/or other like devices configured to emit an audible and/or optical alarm or signal in response to a command or signal from the controller 52. Such an alarm or other signal may be initiated by, for example, the controller 52 when the calculated temperature meets or exceeds a threshold temperature. In additional exemplary embodiments, such an alarm or signal may be initiated during a substantially continuous temperature calculation operation where the rate of patient temperature change meets or exceeds a predetermined temperature change rate threshold.

The controller 52 may be operably connected to the operator interfaces 22, display 54, sensor 32, and/or other components of the temperature probe 10, and the controller 52 may be configured to control the operation of such components. In an exemplary embodiment, the controller 52 may be configured to receive signals, information, measurements, and/or other data from the sensor 32 of the temperature probe 10, and to calculate an estimated core temperature of the patient based on the information received. The controller 52 may also be configured to execute one or more commands and/or control programs. For example, the controller 52 may be programmed to initiate one or more alarms in response to calculating a patient temperature that is greater than or equal to a predetermined threshold temperature. In an exemplary embodiment, such a threshold temperature may be approximately 100° F. In addition, the controller 52 may be configured to initiate such an alarm during a substantially continuous temperature calculation operation if the calculated temperature increases and/or decreases at a rate that is greater than or equal to a predetermined threshold temperature change rate.

The controller 52 may comprise a processor, memory, and/or other known controller components to facilitate the functionality described herein. In an exemplary embodiment, the controller 52 may be disposed within, for example, the handle 20 of the temperature probe 10. In such an embodiment, the handle 20 may form one or more substantially water-tight and/or substantially hermetically sealed compartments for storing the various components of the controller 52.

As shown in FIGS. 1-5, the probe cover 30 may include a body 38, a waveguide 44 extending from the body 38, and an annular flange 34. The body 38 may be substantially conical, substantially cylindrical, and/or any other suitable shape, and in exemplary embodiments, the body 38 may be similar in shape, size, and/or dimensions to the head 18. For example, the probe cover 30 may be hollow, and the body 38 may be incrementally longer than the head 18 so as to fit over substantially the entire head 18. When mounted on the temperature probe 10, the probe cover 30 may overlay the sensor 32 disposed at the tip 16 of the head 18. The probe cover 30 may define an orifice 46 at a proximal end 42 thereof. Similar to the head 18, the probe cover 30 may also include a substantially atraumatic tip 58 at a distal end 40 thereof, and the tip 58 may be formed by the waveguide 44. The probe cover 30 may have a longitudinal axis 76 extending centrally through the body 38, the waveguide 44, and the tip 58, and when the probe cover 30 is connected to the temperature probe 10, the longitudinal axis 76 may be substantially collinear with, for example, a central and/or longitudinal axis (not shown) of the sensor 32. Furthermore, as shown in FIGS. 1-3, in exemplary embodiments, the waveguide 44 may extend along the longitudinal axis 76.

The probe cover 30 may be formed from any medically approved material known in the art. Such materials may include, for example, plastics, polymers, and/or any of the other materials discussed above with regard to the temperature probe 10. Using such materials may enable, for example, the probe cover 30 to be repeatedly used and/or sanitized. Such materials may also facilitate formation of the probe cover 30 through any molding, extrusion, and/or other like process known in the art. Such materials and/or processes may enable the probe cover 30 to be formed with any desirable transmissivity, thickness, dimensions, and/or other configurations. For example, multiple probe covers 30 of the present disclosure may be formed at the same time though the processes discussed above, and each batch or lot of probe covers 30 may be formed with substantially the same transmissivity, thickness, dimensions, and/or other configurations. Although it may be desirable for the probe covers 30 formed in each lot to have identical configurations, such repeatability within the lot may not be possible due to variations and/or imperfections inherent in the above manufacturing processes. Accordingly, the transmissivity, thickness, dimensions, and/or other configurations of the probe covers 30 in each lot may be substantially identical within a desired tolerance range.

In exemplary embodiments, the probe cover 30 may include one or more optical components 56 disposed in the waveguide 44. In an exemplary embodiment, at least one of the optical components 56 may be disposed flush with and/or form at least a portion of the tip 58. The optical components 56 may be similar to the optical components 36 described above with respect to the head 18. For example, the optical components 56 may comprise one or more windows, mirrors, lenses, filters, or other like components, and in an exemplary embodiment, the optical components 56 may comprise one or more divergent, collimating, and/or convergent lenses. Such optical components 56 may assist in focusing, guiding, and/or otherwise directing radiation 62 to the sensor 32. In further exemplary embodiments, such optical components 56 may assist in focusing, guiding, and/or otherwise directing radiation 62 emitted by the sensor 32.

In still further exemplary embodiments, the waveguide 44 itself may function as and/or otherwise comprise an optical component 56. For example, although FIGS. 1-5 illustrate the waveguide 44 as being substantially cylindrical, in additional exemplary embodiments, the waveguide 44 may be substantially conical, substantially concave, substantially convex, tapered, and/or any other known non-cylindrical shape. It is understood that the waveguide 44 may include an inner wall 60 and an outer wall 61, and in exemplary embodiments, the shape and/or other configurations of the inner wall 60 of the waveguide 44 may be the same as or different than the shape and/or other configurations of the outer wall 61 of the waveguide 44. As shown in the exemplary embodiments illustrated in FIGS. 6-9, the inner wall 60 of the waveguide 44 may be, for example, substantially conical, substantially concave, substantially convex, substantially tapered, and/or any other non-cylindrical shape. In such exemplary embodiments, the inner wall 60 of the waveguide 44 may operate as and/or otherwise comprise an optical component 56, and the inner wall 60 may assist in altering the field of view of the sensor 32. For example, the inner wall 60 of such an exemplary waveguide 44 may assist in focusing the radiation 62 as it enters the tip 58. The various configurations of the inner wall 60 may direct the radiation 62 to the sensor 32, thereby, for example, effectively enlarging the field of view of the sensor 32 and improving the radiation collecting capabilities of the system 100. In further exemplary embodiments, the outer wall 61 and/or the inner wall 60 of the waveguide 44 may be, for example, substantially conical, substantially concave, substantially convex, substantially tapered, and/or any other non-cylindrical shape.

Figure 4:
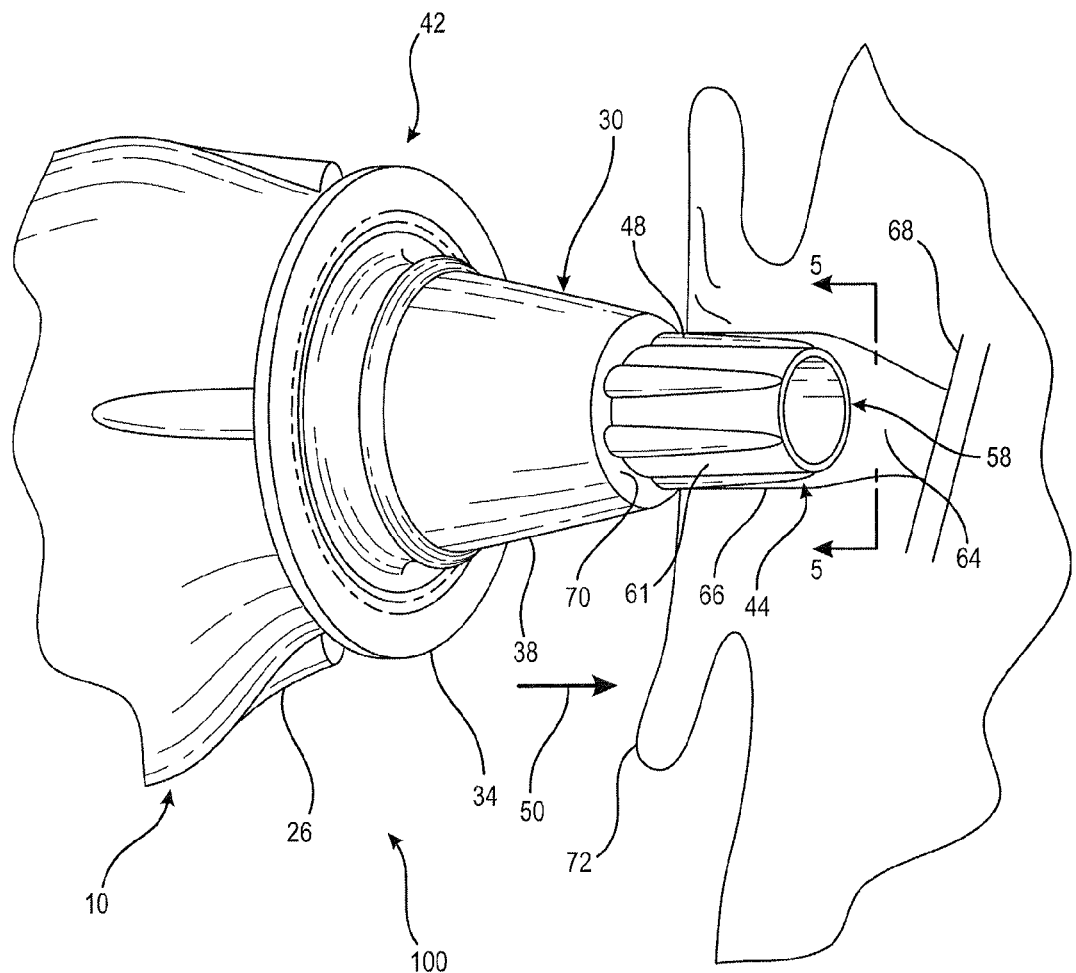
FIG. 4 illustrates a portion of the temperature measurement system shown in FIG. 1.

The optical components 56 described herein may assist in focusing the radiation 62 as it enters and/or exits the tip 58 of the probe cover 30. Such optical components 56 may be selected to desirably widen, narrow, bend, and/or otherwise shape a field of view 64 of the sensor 32. As shown in FIG. 2, the field of view 64 of the sensor 32 may extend distally from the optical component 56 at any desired angle, and may be defined as the area within which radiation 62 emitted by a target may impinge upon the sensor 32. In alternative embodiments, the field of view 64 may also include the area within which radiation 62 emitted by the sensor 32 may impinge upon the target. As shown in FIG. 4, when the tip 58 is disposed within an ear 72 of the patient, such as within the patient's ear canal 66, such a target may be the tympanic membrane 68. The field of view 64 may be two or three-dimensional, and may have any shape and/or size useful in enhancing the sensitivity of the sensor 32. For example, the field of view 64 may be substantially conical, substantially cylindrical, and/or any other shape known in the art. It is understood that various lenses and/or other optical components 56 having different focal lengths, transmissivities, and/or other optical characteristics may be selected for use with the exemplary probe covers 30 of the present disclosure to desirably shape the field of view 64. In exemplary embodiments, various probe covers 30 having different respective fields of view 64 may be used with a single temperature probe 10, and an individual probe cover 30 may be selected for use based on the shape and/or size of its respective field of view 64. For example, obtaining a temperature measurement within the ear canal 66 of a pediatric patient may require the use of a probe cover 30 having a different field of view 64 than a probe cover 30 used to obtain a temperature measurement within the ear canal 66 of an adult patient. In alternative exemplary embodiments, the tip 58 of the probe cover 30 may be substantially open, and in such exemplary embodiments, and the optical component 56 may be omitted. Additionally, in such exemplary embodiments, the field of view 64 may be shaped based on the shape, dimensions, and/or configurations of the body 38, waveguide 44, and/or tip 58.

The waveguide 44 may extend from the distal tip 58 of the probe cover 30 to an annular shoulder 70 of the body 38. For example, the waveguide 44 may be substantially cylindrical, substantially conical, and/or any other shape useful in directing radiation 62 to the sensor 32. A proximal end 78 of the waveguide 44 may be disposed adjacent to the shoulder 70, and the waveguide 44 may be formed integrally with the shoulder 78 and/or the body 38. In such exemplary embodiments, the probe cover 30 may have a substantially one-piece construction, and the waveguide 44 may be formed from the same material as the body 38 and/or the shoulder 70. Alternatively, in additional exemplary embodiments, the waveguide 44 may be adhered, molded, welded, and/or otherwise connected to the shoulder 70 at the proximal end 78. In such alternative embodiments, the waveguide 44 may be made from one or more different materials than the body 38 and/or the shoulder 70.

In exemplary embodiments, the waveguide 44, shoulder 70, and/or body 34 may be made from an infrared transparent material, such as any of the plastics, polymers, and/or other materials discussed above with respect to the probe cover 30. In exemplary embodiments, the inner wall 60 of the waveguide 44 may include a different material than a remainder of the waveguide 44. For example, the inner wall 60 may be at least partially coated with and/or made from a different material than the outer wall 61. In such exemplary embodiments, the inner wall 60 may be coated with and/or otherwise covered by an infrared reflective material such as one or more metals, alloys, paints, dyes, and/or other known reflective materials. In such exemplary embodiments, the infrared reflective material may be a film, coating, and/or other like layer disposed on the inner wall 60 of the waveguide 44. Such reflective materials may be, for example, co-extruded, co-molded, and/or otherwise formed integrally with the waveguide 44. Alternatively, such reflective materials may be disposed on the inner wall 60 once the waveguide 44 has been formed. Such reflective materials may assist in directing radiation 62 to the sensor 32 upon entering the waveguide 44 through the tip 58 and/or the optical component 56.

As shown in FIG. 2, the inner wall 60 may have a first diameter D1 less than a second diameter D2 of the outer wall 61. The waveguide 44 may extend substantially perpendicular from the shoulder 70, and may have any height H desired. The height H may be tailored to the particular anatomical constraints of the patient for which the probe cover 30 is intended to be used. For example, pediatric patients may have shorter ear canals 66 than adult patients. Accordingly, a probe cover 30 tailored for use with a pediatric patient may include a waveguide 44 having a height H less than a corresponding height of a waveguide 44 designed for use with an adult patient. The height H of such waveguides 44 may be selected to maintain a minimum distance between the distal tip 58 and, for example, the eardrum, tympanic membrane 68, and/or any other portion of the patient's ear 66 while the tip 58 is disposed within the ear 66. For example, during use the waveguide 44 may be inserted into the ear canal 66 in the direction of arrow 50 (FIG. 4) until the shoulder 70 abuts the ear 72 of the patient, external to the ear canal 66, such that a desired minimum distance between the tip 58 of the probe cover 30 and the eardrum (not shown) of the patient is maintained. Maintaining such a desired minimum distance may prevent damage to the eardrum, and such a minimum distance may be equal to approximately 1 cm or greater. The annular shoulder 70 may have a diameter larger than the diameter D2 of the outer wall 61 and of the ear canal 66, and the shoulder 70 may have any desirable width W to prohibit insertion of the shoulder 70 into the ear canal 66. In such a configuration, the shoulder 70 may act as a stop, limiting insertion of the waveguide 44 into the ear canal 66. The shoulder 70 may extend substantially perpendicular from the longitudinal axis 76 to assist in limiting insertion of the waveguide 44.

In an exemplary embodiment, the probe cover 30 may include at least one rib 48 disposed on the waveguide 44. The rib 48 may be disposed at any location on the outer wall 61, and may have any shape, size, orientation, and/or other configuration. For example, the rib 48 may extend along the outer wall 61 substantially parallel to the longitudinal axis 76. The rib 48 may extend along only a portion of the outer wall 61, or alternatively, the rib 48 may extend along the entire height H of the waveguide 44 from the distal tip 58 of the probe cover 58 to the proximal end 78 of the waveguide 44. The rib 48 may have any atraumatic shape known in the art, and may have a substantially rounded, curved, and/or otherwise smooth outer surface so as not to cause damage to the ear canal 66 upon insertion of the waveguide 44. For example, an outer surface of the rib 44 may have any desired radius to avoid damaging the ear canal 66 during use. In still further exemplary embodiments, the rib 48 may be tapered in any desirable direction. For example, the rib 48 may taper away from the longitudinal axis 76 from proximate the distal tip 58 of the probe cover 30 toward the proximal end 78 of the waveguide 44. As shown in FIG. 2, with such a tapered configuration, the waveguide 44 may have a maximum diameter D3 proximate the shoulder 70 and the proximal end 78. In exemplary embodiments, the diameter D3 may be greater than the diameter of the patient's ear canal 66, and such a tapered configuration may further assist in limiting insertion of the waveguide 44 into the ear canal 66.

It is understood that, as shown in FIGS. 1-9, exemplary embodiments of the probe cover 30 may include a plurality of ribs 48 spaced circumferentially around the outer wall 61 of the waveguide 44, and each rib 48 of the plurality of ribs may have any of the configuration described above. For example, each rib 48 may extend substantially parallel to the longitudinal axis 76 along substantially the entire height H of the waveguide 44. Although the ribs 48 are shown as being substantially linear, in additional exemplary embodiments, the ribs may comprise rounded knobs, mounds, extensions, spiral threads, and/or any other structures configured to space the outer wall 61 from the ear canal 66. For example, the ribs 44 may assist in forming a gap 74 (FIG. 5) between the outer wall 61 of the waveguide 44 and the ear canal 66 during use. For example, the ribs 44 may space the outer wall 61 of the waveguide 44 from the ear canal 66 so as to substantially thermally insulate the waveguide 44 from the ear canal 66. Insulating the waveguide 44 in this way may assist in increasing the accuracy of temperature measurements obtained by the sensor 32.

The probe cover 30 may also include one or more structures to facilitate usage with, connection to, and/or removal from the temperature probe 10. For example, while the orifice 46 may be shaped, sized, and/or otherwise configured to accept the head 18 and to mate with one or more ejector mechanisms 26 of the temperature probe 10, in further exemplary embodiments, at least a portion of the proximal end 42 of the probe cover 30 may include additional notches, cutouts, tabs, ribs, flanges, and/or other retention components 80 configured to assist in connecting the probe cover 30 to and/or disconnecting the probe cover 30 from the temperature probe 10. The head 18 may also include one or more ribs, flanges, knobs, lips, and/or other like retention components 28 proximate the base 24, and the corresponding retention components 80 of the probe cover 30 may be shaped, sized, located, and/or otherwise configured to mate with the retention components 28 of the head 18. Once the probe cover 30 has been connected to the temperature probe 10, the retention components 80 of the probe cover 30 may assist in providing a retention force sufficient to maintain the connection between the probe cover 30 and the temperature probe 10. An exemplary retention force may be a compression force applied by, for example, a semi-circular and/or otherwise concave retention component 80 of the probe cover 30 to one or more convex retention components 28 proximate the base 24 of the head 18.

The probe cover 30 may also include, for example, an annular flange 34 disposed at the proximal end 42. The flange 34 may surround the body 38 at the proximal end 42 of the probe cover 30, and may form part of the one or more retention components 80. Alternatively, the flange 34 may be disposed proximate the one or more retention components 80 such as, for example, proximal to the retention components 80. At least a portion of the flange 34 may extend substantially perpendicular to the longitudinal axis 76, and as shown in FIG. 2, an exemplary embodiment of the flange 34 may include one or more camming surfaces 84 positioned such that the ejector mechanism 26 is able to ride along the one or more camming surfaces 84 in the direction of arrow 86. Such movement of the ejector mechanism 26 may assist in bending and/or otherwise flexing a portion of the probe cover 30. The force applied by the ejector mechanism 26 to the one or more camming surfaces 84 of the probe cover 30 may be sufficient to overcome the retention force provided by the retention components 80, and as a result, the probe cover 30 may be ejected from the head 18.

Figure 5:
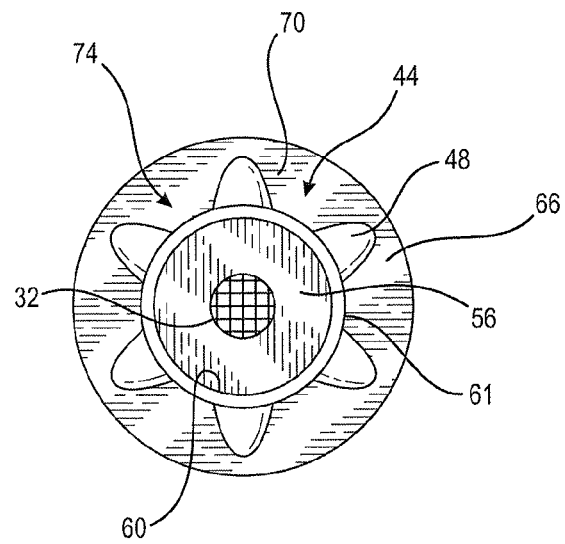
FIG. 5 is another view of the portion of the temperature measurement system shown in FIG. 4.
Figure 6:
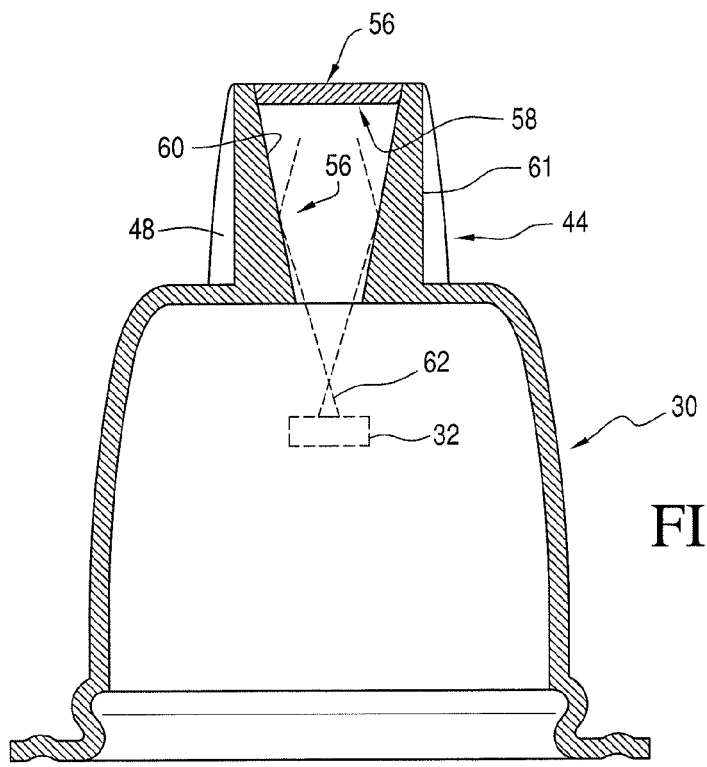
FIG. 6 illustrates a cross-sectional view of an exemplary probe cover of the present disclosure.
Figure 7:
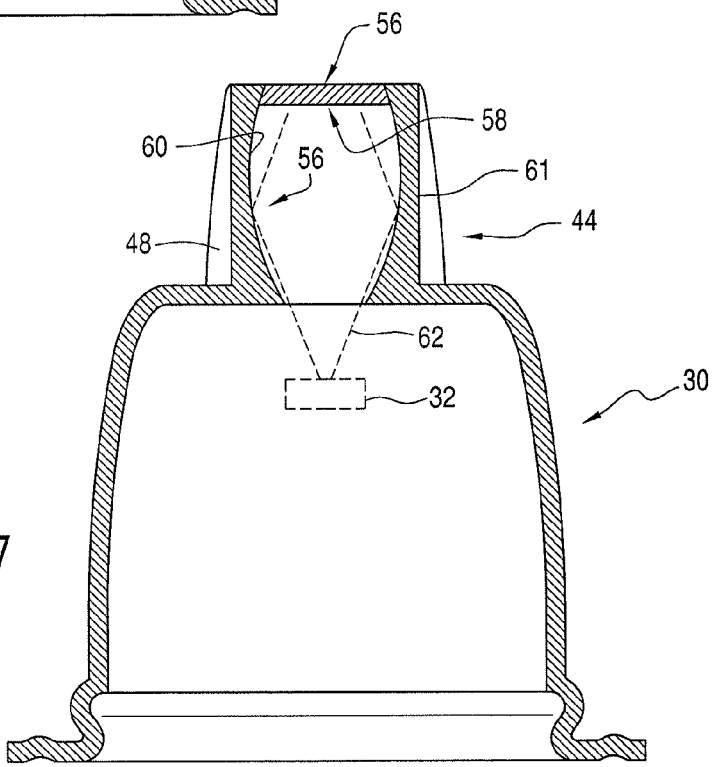
FIG. 7 illustrates a cross-sectional view of another exemplary probe cover of the present disclosure.
Figure 8:
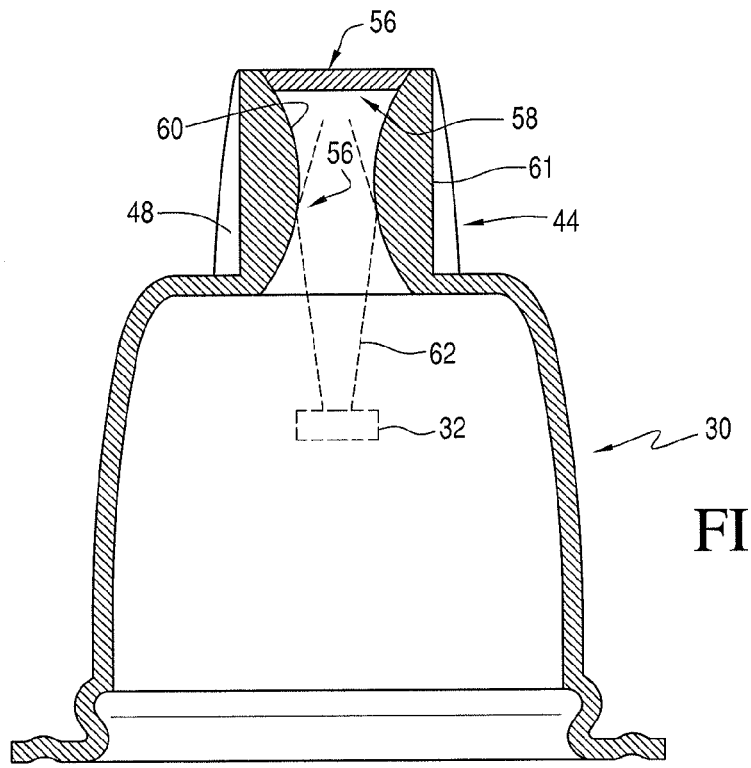
FIG. 8 illustrates a cross-sectional view of yet another exemplary probe cover of the present disclosure.
Figure 9:
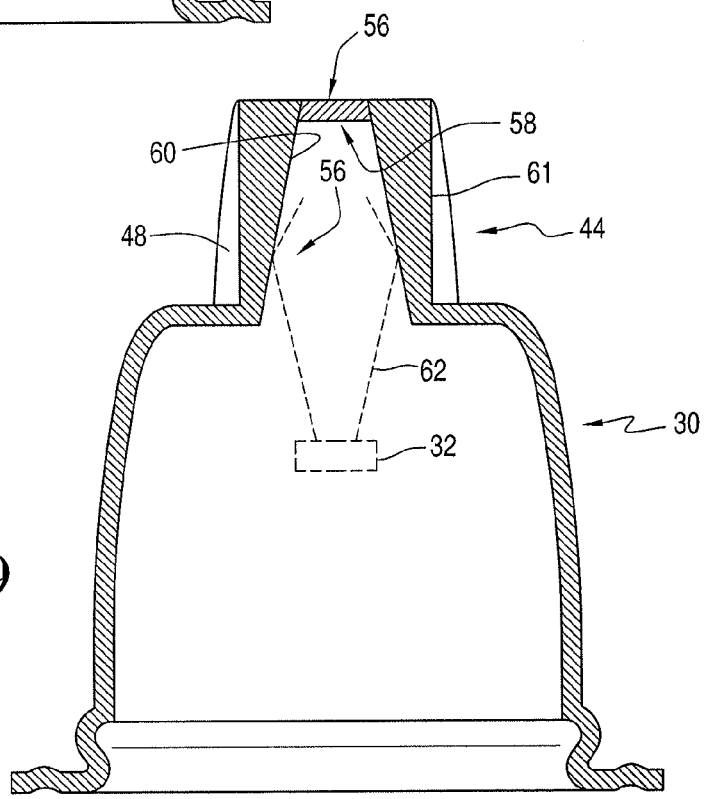
FIG. 9 illustrates a cross-sectional view of a further exemplary probe cover of the present disclosure.

As shown in FIG. 5, an exemplary temperature measurement system 100 of the present disclosure may include an exemplary temperature probe 10 and at least one of the removably attachable probe covers 30 described herein. Such an exemplary temperature measurement system 100 may also include a plurality of removably attachable probe covers 30 having different shapes, sizes, and/or configurations. For example, each probe cover 30 of the plurality of probe covers may include a substantially cylindrical waveguide 44 having a different outer diameter D2. Such an exemplary temperature measurement system 100 may be configured to assist in calculating, estimating, and/or otherwise determining the core temperatures of different patients, each having ear canals 66, tympanic membranes 68, and/or ear drums of various shapes, sizes, and configurations. Such patients may include, for example, infant, pediatric, adolescent, adult, and/or geriatric patients. During use of such an exemplary temperature measurement system 100, an appropriate probe cover 30 may be selected for use with the temperature probe 10 based on the dimensions of the waveguide 44 and, for example, the specific anatomical constraints of the respective patient's ear canal 66.

The temperature probes 10 and probe covers 30 described herein may be utilized by physicians, nurses, and/or other health care professionals in a variety of different environments. For example, the devices and/or the temperature measurement systems described herein may be employed in any of a number of examination facilities to determine one or more temperatures associated with a patient such as, for example, an estimated core temperature of the patient. Such an estimated core temperature may be utilized by the health care professional to assist in treating the patient, and may have a variety of uses that are well known in the medical field.

In order to determine a patient temperature according to an exemplary embodiment of the present disclosure, a user of the temperature probe 10 may insert the temperature probe 10 into a probe cover 30. For example, the user may insert at least a portion of the temperature probe 30 such as, for example, the head 18 into the probe cover 30, via the orifice 46. In an exemplary embodiment, the probe cover 30 may be disposed within a box or other like storage container (not shown) while the head 18 of the temperature probe 10 is inserted into the probe cover 30. In such an exemplary embodiment, the probe cover 30 may be accessed through an opening of the storage container for insertion of the head 18.

As one or more of the retention components 28 of the temperature probe 10 comes into contact with the probe cover 30, the retention components 28 may hook, clip, and/or otherwise mate with the proximal end 42 of the probe cover 30 to assist in retaining the probe cover 30 on the head 18. In exemplary embodiments in which the proximal end 42 of the probe cover 30 defines one or more of the notches, cutouts, and/or other concave retention components 80 described above, these retention components 80 may mate with the corresponding retention components 28 of the temperature probe 10 to assist in retaining the probe cover 30 thereon.

Once the probe cover 30 has been mounted onto the head 18 of the temperature probe 10, the probe cover 30 may be inserted into a body cavity of a patient to facilitate determining an estimated core temperature of the patient. For example, as shown in FIG. 4, the waveguide 44 may be inserted into the ear canal 66 of the patient such that the tip 58 is disposed proximate the tympanic membrane 68. The probe cover 30 and/or the sensor 32 (FIG. 2) may be positioned such that the tympanic membrane 68 is disposed at least partially within the field of view 64 of the sensor 32. As described above, the waveguide 44 may be selected for use based on the specific anatomical constraints of the patient, and based on the height H, diameters D1, D2, and/or other configurations of the waveguide 44. For example, with pediatric patients, a waveguide having a relatively small diameter D2 may be selected such that the waveguide 44 may fit within the smaller ear canal 66 of the patient. Additionally, with such patients, a waveguide 44 having a relatively small height H may be selected so as to avoid contacting or damaging the tympanic membrane 68 or the eardrum of the patient upon insertion of the waveguide 44. It is understood that the shoulder 70 may be sized, located, and/or otherwise configured to maintain a desired minimum distance between such anatomical structures and the tip 58 of the probe cover 30.

Moreover, with such pediatric patients, a waveguide 44 producing a desired field of view 64 for the sensor 32 may be selected. Such a field of view 64 may result from the particular dimensions, configurations, and/or one or more optical components 56 of the waveguide 44. For example, the field of view 64 of the waveguide 44 selected for a pediatric patient may be wider or narrower than a corresponding field of view produced by a standard non-waveguide probe cover. In particular, a waveguide 44 of the present disclosure may focus the field of view 64 to maximize the amount of radiation 62 collected by the sensor 32 from and/or emitted by the tympanic membrane 68 of a pediatric patient. In such exemplary embodiments, the waveguide 44 may also focus the field of view, for example, away from the ear canal 66, thereby minimizing the amount of radiation 62 collected by the sensor 32 from and/or emitted by the ear canal 66. Maximizing the amount of radiation 62 collected by the sensor 32 from the tympanic membrane 68 may assist in increasing the accuracy of the core temperature calculation, and may reduce the error associate with such calculations. Although described in the present example with regard to a pediatric patient, as described above, the various probe covers 30 of the present disclosure may be tuned for use with infants, pediatric patients, adolescent patients, adult patients, and/or geriatric patients, each of whom may have different respective anatomical constraints. It is also understood that each of the exemplary probe covers 30 described herein may be shaped, sized, and/or otherwise configured to attach to the same head 18 regardless of their intended use or target patient.

To further reduce error associated with such core temperature calculations, the one or more ribs 48 disposed on the waveguide 44 may space the outer wall 61 of the waveguide 44 from the ear canal 66. For example, as shown in FIG. 5, the gap 74 formed between the outer wall 61 and the ear canal 66 may substantially thermally insulate the waveguide 44 from the ear canal 66. The ribs 48, and the corresponding gap 74, may minimize the transmission of thermal energy from the ear canal 66 to the waveguide 44 during use. As a result, the temperature of the ear canal 66 may have a negligible effect on the sensed temperature of the tympanic membrane 68 and on the resulting core temperature calculations.

Once the waveguide 44 has been desirably positioned within the ear canal 66, the sensor 32 may be activated via the operator interfaces 22 to sense a temperature indicative of a temperature of the body cavity. For example, in an embodiment in which the sensor 32 comprises a thermocouple and/or a thermistor, the sensor 32 may be utilized to measure the temperature of the body cavity. Alternatively, in embodiments in which the sensor 32 comprises an infrared temperature sensor, the sensor 32 may detect radiation 62 emitted by the body cavity of the patient. For example, radiation 62 emitted by the tympanic membrane 68 may be directed to the sensor 32 for collection via the waveguide 44 and/or the one or more optical components 56. In further exemplary embodiments, such radiation 62 may be reflected and/or reemitted by the tympanic membrane 68, and at least some of the reflected and/or reemitted radiation may be collected by the sensor 32. It is understood that such radiation 62 may return to the sensor 32 for collection via the optical components 56 and/or the waveguide 44.

Signals indicative of the measured tympanic membrane temperature may be sent to the controller 52 by the sensor 32, and the controller 52 may assist in estimating the core temperature based on the sensed temperature. In additional exemplary embodiments, the controller 52 may estimate the core temperature based on the signals received from the sensor 32 as well as information related to the configuration of the waveguide 44. For example, the height H, diameters D1, D2, D3, transmissivity, and/or material composition of the waveguide 44 may be incorporated as an input to a core temperature calculation algorigthm used by the controller 52. In addition, the reflectivity, material composition, and/or other characteristics of the one or more coatings disposed on the inner wall 60, as well as the shapes, dimensions, locations, and/or quantity of the ribs 48 disposed on the outer wall 61 may be incorporated as inputs to such an algorithm. Any of the above inputs may be utilized in the core temperature calculation to reduce error. As discussed above, such error is commonly associated with the particular anatomical constraints of the particular patient, the position of the tympanic membrane 68 relative to the field of view 64, and/or the transmission of thermal energy from the ear canal 66 to the waveguide 44. Once the estimated core temperature of the patient has been calculated by the controller 52, the display 54 may communicate the temperature to a user of the temperature probe 10.

Additional exemplary embodiments of the present disclosure may employ further techniques to assist in reducing the error associated with calculating the core temperature of the patient. For example, one such method of core temperature determination may include heating at least a portion of the temperature probe 10 to a known temperature, and calculating the core temperature based on the sensed temperature described above as well as the known temperature. In exemplary embodiments, the known temperature to which a portion of the temperature probe 10 may be heated may be between approximately 90° F. and approximately 100° F. For example, the known temperature may be between approximately 92° F. and approximately 93° F., and/or within any other useful temperature range. It is understood that one or more heaters (not shown) may be utilized to assist in heating the portion of the temperature probe 10 to this known temperature.

In still further exemplary embodiments, one or more additional sensors (not shown) may be disposed on the temperature probe 10 at a location useful for detecting the presence of the probe cover 30. For example, such additional sensors may be disposed proximate the base 24 of the head 18 and configured to detect the proximal end 42 of the probe cover 30 once the head 18 has been inserted into the probe cover 30. In still further exemplary embodiments, such sensors 28 may be disposed proximate the tip 16 and configured to detect the distal end 40 of the probe cover 30 once the head 18 has been inserted into the probe cover 30. In such exemplary embodiments, the one or more additional sensors may comprise, for example, a proximity sensor and/or any other like sensing device, and sensing the temperature indicative of the body cavity temperature may be performed in response to detecting the presence of the probe cover 30 on the head 18.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A temperature measurement system, comprising:
a temperature probe including a head and an infrared temperature sensor disposed in the head; and
a replaceable probe cover removably attachable to the head, the probe cover including a body, a substantially cylindrical waveguide, a shoulder disposed between the waveguide and the body, and a distal tip,
the shoulder extending from the waveguide away from a longitudinal axis of the probe cover, and being disposed distal to a distal-most end of the head when the probe cover is attached to the head, and
the waveguide being configured to direct radiation entering the distal tip to the temperature sensor when the probe cover is attached to the head, wherein the waveguide extends substantially perpendicularly from the shoulder to the distal tip of the probe cover, the shoulder extending substantially perpendicular from the longitudinal axis and having a larger diameter than the waveguide.

2. The system of claim 1, wherein the waveguide includes an inner wall and an infrared reflective material disposed on the inner wall.

3. The system of claim 2, wherein the waveguide and the body are made from an infrared transparent material.

4. The system of claim 2, wherein the inner wall is non-cylindrical.

5. The system of claim 1, wherein the waveguide includes an outer wall, and a rib on the outer wall extending substantially parallel to the longitudinal axis of the probe cover.

6. The system of claim 5, wherein the rib extends from the distal tip of the probe cover to a proximal end of the waveguide.

7. The system of claim 5, wherein the rib tapers away from the longitudinal axis from proximate the distal tip of the probe cover toward a proximal end of the waveguide.

8. The system of claim 5, wherein the waveguide includes a plurality of ribs spaced circumferentially around the outer wall, each rib of the plurality of ribs extending substantially parallel to the longitudinal axis and having a curved outer surface.

9. The system of claim 1, further including a plurality of probe covers removably attachable to the head, wherein each probe cover of the plurality of probe covers includes a substantially cylindrical waveguide having a different outer diameter.

10. The system of claim 1, wherein the shoulder comprises an annular shoulder extending circumferentially around the longitudinal axis of the probe cover.

11. The system of claim 1, further including a lens disposed at the distal tip of the probe cover, the lens configured to assist in directing the radiation to the infrared temperature sensor as the radiation enters the waveguide.

12. A temperature measurement system, comprising:
a probe cover configured for use with a temperature probe having a head and an infrared temperature sensor disposed in the head, the probe cover including
a hollow substantially conical body having a central longitudinal axis,
a substantially cylindrical waveguide extending along the longitudinal axis,
a shoulder disposed between the waveguide and the body, the shoulder extending from the waveguide away from the longitudinal axis and being disposed distal to a distal-most end of the head when the probe cover is attached to the head, and
a substantially atraumatic distal tip,
the waveguide having an inner wall and an infrared reflective material disposed on the inner wall, the infrared reflective material being configured to direct radiation entering the distal tip to the temperature sensor, wherein the shoulder comprises an annular shoulder extending substantially perpendicularly from the longitudinal axis at a proximal end of the waveguide, the shoulder having a diameter larger than an outer diameter of the waveguide.

13. The system of claim 12, wherein the waveguide further includes an outer wall and a plurality of ribs spaced circumferentially around the outer wall, each rib of the plurality of ribs extending substantially parallel to the longitudinal axis.

14. The system of claim 12, wherein the probe cover further includes a lens disposed at the distal tip, the lens configured to assist in directing the radiation to the infrared temperature sensor as the radiation enters the waveguide.

15. The system of claim 14, wherein the probe cover further includes an annular flange disposed at a proximal end of the probe cover, the flange having a camming surface configured to mate with an ejector mechanism of the temperature probe.

16. The system of claim 14, wherein the probe cover further includes a first retention component configured to mate with a second retention component of the temperature probe.

17. The system of claim 12, wherein the inner wall of the waveguide comprises an optical component.

18. A method of determining a temperature of a patient, comprising:
   attaching a removable probe cover to a head of a temperature probe, the probe cover including:
      a distal end,
      a substantially cylindrical waveguide disposed at the distal end,
      a substantially conical body having a central longitudinal axis, and
      a substantially annular shoulder disposed between the waveguide and the body,
         the shoulder extending substantially perpendicularly from the longitudinal axis at a proximal end of the waveguide, the shoulder having a diameter larger than an outer diameter of the waveguide,
         the body extending proximally from the shoulder, and
         the shoulder being disposed distal to a distal-most end of the head when the probe cover is attached to the head;
   inserting the waveguide into an ear canal of the patient;
   collecting infrared radiation passing from a tympanic membrane of the patient to a sensor disposed within the head of the temperature probe, wherein a portion of the infrared radiation is directed to the sensor upon reflecting off of an inner wall of the waveguide; and
   determining the temperature of the patient based on the collected radiation.

19. The method of claim 18, further including abutting the shoulder of the probe cover against an ear of the patient, external to the ear canal, such that a desired minimum distance between a tip of the probe cover and an eardrum of the patient is maintained.

20. The method of claim 18, further including spacing an outer wall of the waveguide from the ear canal, with a rib disposed on the outer wall, such that the waveguide is substantially thermally insulated from the ear canal.

21. The method of claim 18, wherein the radiation passes from the tympanic membrane of the patient to the sensor via a converging lens disposed at a distal tip of the probe cover.

22. The system of claim 1, wherein the body extends proximally from the shoulder to a flange disposed at a proximal end of the probe cover, and wherein the shoulder forms at least a portion of an outer surface of the probe cover.

23. The system of claim 1, wherein the waveguide includes an outer wall, and a rib on the outer wall extending substantially parallel to the longitudinal axis.

* * * * *